Figure 1:
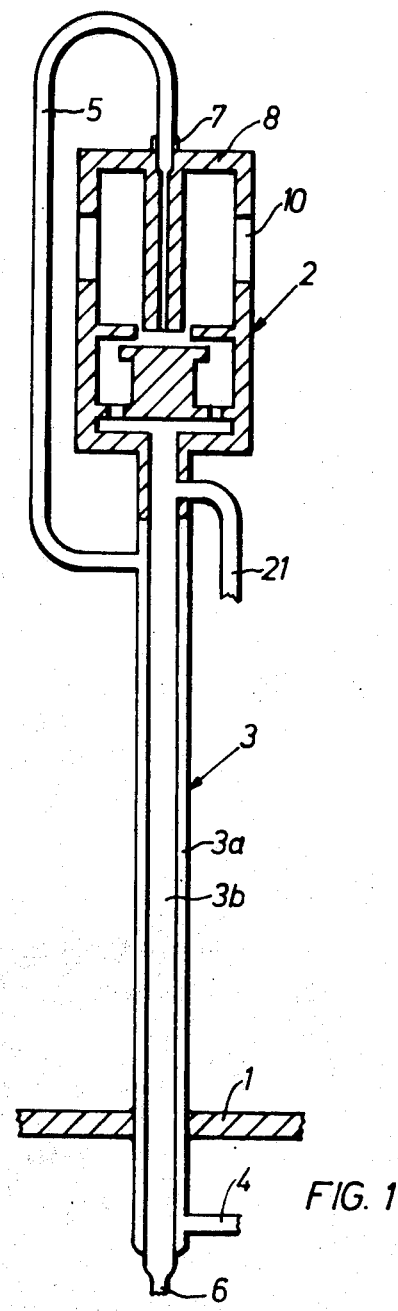

United States Patent [19]

Becker et al.

[11] 4,061,467
[45] Dec. 6, 1977

[54] PROCESS AND APPARATUS FOR THE REMOVAL OF SAMPLES FOR ANALYSERS FROM A STREAM OF EXHAUST GAS

[75] Inventors: Wolf-Jürgen Becker; Wolfram Breuer; Klaus Siemer, all of Leverkusen, Germany

[73] Assignee: Bayer Aktiengesellschaft, Leverkusen, Germany

[21] Appl. No.: 617,219

[22] Filed: Sept. 26, 1975

[30] Foreign Application Priority Data

Sept. 28, 1974 Germany .............................. 2446404

[51] Int. Cl.² .............................................. G01N 1/22
[52] U.S. Cl. .............................. 23/232 R; 23/254 R; 73/421.5 R
[58] Field of Search ............. 23/232 R, 232 E, 254 R, 23/254 E, 255 R, 255 E; 73/421.5 R, 421.5 A

[56] References Cited

U.S. PATENT DOCUMENTS

| | | | |
|---|---|---|---|
| 3,249,403 | 5/1966 | Bochinski et al. | 23/254 R |
| 3,883,739 | 5/1975 | Jenkins | 23/254 E |

*Primary Examiner*—R.E. Serwin
*Attorney, Agent, or Firm*—Burgess, Dinklage & Sprung

[57] ABSTRACT

In a process for the removal of samples from flue gases or other highly concentrated exhaust gases, before the sample is removed from the main stream of exhaust gas it is diluted with a carrier gas which is free from this exhaust gas. The sample is diluted in the main stream of exhaust gas by a carrier gas introduced from outside. The diluted sample can then be analyzed in conventional gas analyzers.

4 Claims, 4 Drawing Figures

PROCESS AND APPARATUS FOR THE REMOVAL OF SAMPLES FOR ANALYSERS FROM A STREAM OF EXHAUST GAS

This invention relates to a method for the removal of samples from flowing exhaust gases for the purpose of analysis. The invention relates also to apparatus for carrying out the method.

Devices for removing gas samples, which operate on the principle of dilution, mix the gas to be analysed with a purified carrier gas and thereby dilute it to such an extent that the concentrations of solid, liquid and condensing impurities are reduced to a level at which they do not affect the process of analysis, especially in continuously measuring automatic gas analysis apparatus. The reason for taking this measure is that many commercially available gas analysis apparatus are very sensitive to the presence of dirt in the measuring system. If impure gases or exhaust gases are diluted with dry, clean gas in a constant, clearly specified ratio, the amount of dirt entering the measuring system is substantially reduced.

Most continuously measuring automatic gas analysers are sensitive to contamination of the measuring system with solid, liquid or condensing substances. Numerous gas sampling devices have therefore been brought on the market by various manufacturers with the object of eliminating these impurities from the gas to be measured (1) H. Karthaus and H. Engelhardt "Physikalische Gasanalyse" Grundlagen publication L 3410 of Hartman & Braun AG Frankfurt (1971) p. 7/8 and 82–105, 2) fur Fur und and Regeln in der Wärme- und Chemietechnik, Munich (1962)). The devices most commonly used nowadays for removing impurities are ceramic filters arranged inside or outside an exhaust gas flue (3) A. Naumann "Entnahmetechnik und andere Voraussetzungen fur die erfolgreiche Anwendung von Analysengeräten" VDI-Berichte No. 97 (1966) 39/49, 4) W. Breuer "Die Meβtechnik bei der Reinhaltung der Luft",VDI-Zeitschrift 107 (1965) 30, 1434/38, 5) H.W. Thoenes, W. Guse "Neuester Stand der Entwicklung von Kontrollmeβgeräten zur Dauerüberwachung von Gas-Emissionen, Staub-Reinhalt. Luft 28 (1968) 3, 128/134, 6) K. Jander "Messung von Schwefeldioxid-Emissionen mit dem URAS 1" Gesundheits-Ingenieur 93 (1972) 2, 52/56.

These filters serve to filter off flakes of soot and course dust particles. The filters are in most cases directly connected to a water cooler with automatic separator which depresses the dewpoint of the gas to be analysed below the temperatures occurring in the following pipes. The pre-dried gas can now be carried for several metres in flexible tubes to an analysis apparatus chamber. The removal of fine dust, however, requires an additional fine filter at this stage. The pre-dried gas must then generally be completely dired or adjusted to a constant water vapour content to which the analysis apparatus is calibrated. Other auxiliary devices and additives may also be necessary to deal with other impurities.

These gas sampling devices and accessories have only a limited service life because they are liable to get blocked up and suffer other kinds of damage and must therefore be constantly kept in repair. Qualified service personnel are necessary for monitoring such installations. Contamination of the measuring system is greater reduced by diluting the impure gas with dry, clean gas at a constant, clearly specified ratio. This method is known and also used in practice. Dilution of the gas to be measured has in the past in most cases been carried out in a separate apparatus after the sample has been removed. In the simplest case, such a dilution apparatus consists of a mixing vessel into which are introduced a stream of the measuring gas and a stream of dry, clean gas at a certain ratio to each other and from which the mixture can be removed. The impure gas is directly taken from a flue or exhaust gas conduit by a sampling device which is thus liable to get soiled and blocked up and therefore requires regular servicing. Special processes and apparatus have been developed to reduce the amount of servicing required and increase the service life of the sampling device.

It is an object of this invention substantially to improve the service life of automatic emission and operational analysers used for the analysis of exhaust air and to enable immision analysers to be used commercially.

According to the invention there is provided a method for the removal of samples for the purpose of analysis from a stream of exhaust gas, wherein the stream of exhaust gas is diluted with a carrier gas which is free from the gas to be analysed before the sample is removed from the stream of exhaust gas.

The sample is thus not drawn from the main stream and diluted outside it as has hitherto been customary but diluted in the main stream itself.

The difficulties of present-day emission measuring techniques listed above can to a large extent be overcome by using a gas sampling device with which the sample of gas is directly diluted in the flue. Most of the emission measuring apparatus at present available can then be used for emission measurements. Numerous other components which cannot be analysed with emission measuring apparatus can be determined by means of commercially available automatic, continuous emission measuring apparatus. For such apparatus, the gas must be diluted to such an extent that it cannot soil the dilution installation and conduits through which it flows. Any chemical reactions between the components in the sample of gas are considerably attenuated by dilution and the accuracy of measurement is thereby increased.

Figure 2:
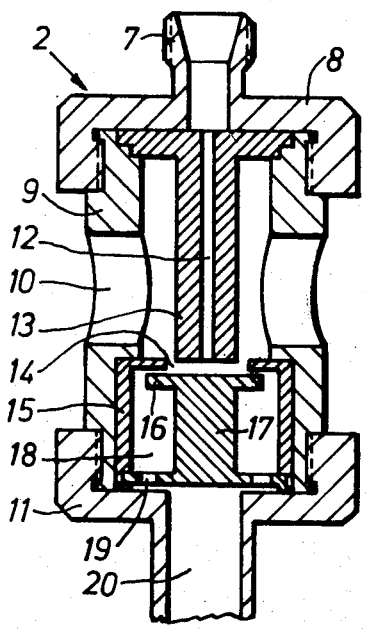

Three different apparatus for carrying out the process according to the invention will now be described in more detail with reference to constructional examples and drawings. FIG. 1 shows a dilution sampling device operating on the principle of a jet pump FIG. 2 represents the jet pump head of the dilution sampling device of FIG. 1

Figure 3:
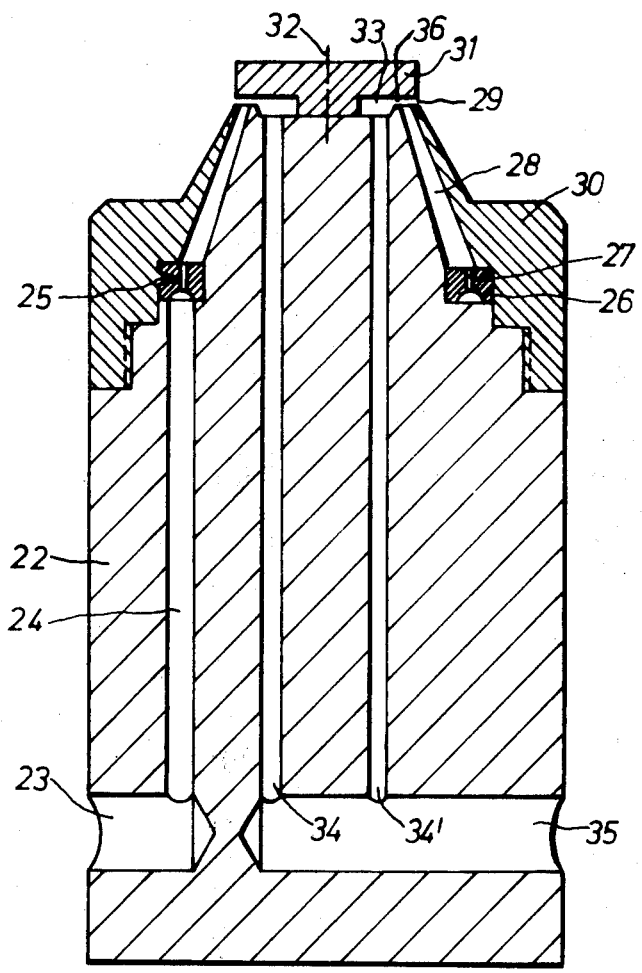
Figure 4:
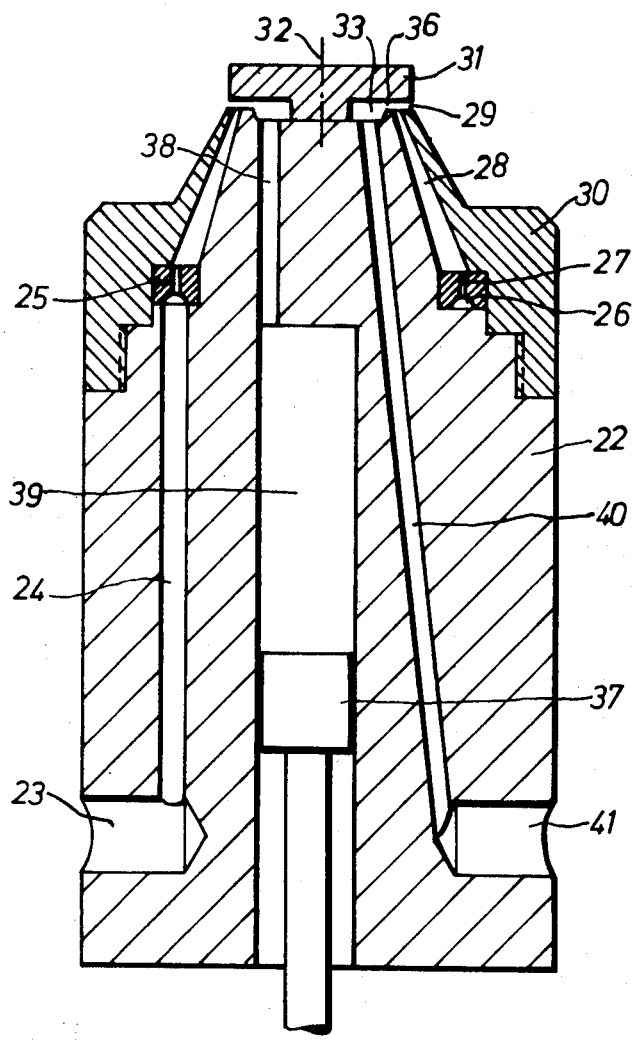

FIG. 3 shows a dilution sampling device operating on the diffusion principle and FIG. 4 shows a dilution sampling device operating on the principle of periodic dilution.

1. Dilution sampling device operating on the principle of a jet pump.

1.1 Principle of dilution

In a first apparatus, a jet pump or ejector is installed inside a flue to dilute the exhaust gas. Known applications of jet pumps include bunsen burners, water jet pumps and locomotive blast pipes. The carrier gas used for operating the jet pump is air which is free from the gas to be analysed. The sudden drop of pressure which occurs in a gas when the tube through which it flows suddenly widens out is utilised in the jet pump to suck in the surrounding gas (exhaust gas) and carry it forwards.

The carrier gas supplied from a nozzle is vigorously mixed with the exhaust gas.

The dilution sampling device (jet pump) is situated inside a flue so that the main stream of exhaust gas flows directly over the intake apertures. Part of the resulting gas mixture is removed through a discharge conduit by a pump and carried to a suitable analyser. Most of the gas mixture is directly carried off into the flue so that pressure fluctuations have little effect on the operating conditions, (degree of dilution).

In many cases, the degree of dilution of a simple jet pump is so great that it must be substantially reduced by special measures. The preferred measure consists of arranging a baffle plate in front of the nozzle opening of the air jet. This causes the air jet to fan out that the degree of dilution can be reduced to from 1:10 to 1:100, depending on the distance of the baffle plate from the nozzle opening 1.2 Practical example An example of a dilution sampling device operating on the principle of a jet pump is shown in FIG. 1. The sampling device is introduced directly into the stream of exhaust gas through an opening in the flue which is then closed by a flange plate 1 on the device. A jet pump head 2 (FIG. 2) is attached to a double walled tube 3. The carrier gas which is free from the gas to be analysed is fed into the outer part 3a of the double-walled tube 3 at 4 and passed through a carrier gas feed pipe 5 to be introduced into the jet pump head 2 through a connection 7 in a cover 8. Dilution of the sample takes place inside the pump head 2. The diluted sample is removed from the inner part 3b of the double-walled tube 3 at 6.

The jet pump head 2 (FIG. 2) consists of a cylinder 9 with four or more intake apertures 10 through which the exhaust gas is taken from the flue by suction. The cylinder 9 is screwed into a flange 11 (similar to sampling cover 8) which is welded to the double-walled tube 3. The endface of the jet pump head is formed by the cover 8 which is screwed to the cylinder 9.

The carrier gas entering the jet pump head 2 through the connection 7 flows through the bore 12 of the nozzle head 13 to enter the interior of the jet pump head 2. The sudden increase in cross-section at the entry into the pump head 2 from the bore 12 causes exhaust gas to be sucked through the openings 10 and carried along by the carrier gas. An opening 14 in a cylinder 15 serves to limit this increase in cross-section. The quantity of exhaust gas taken in and hence the degree of dilution can be varied by altering the intake cross-section 14. After passing through this increased cross-section, the gas mixture streams against a baffle plate 16 mounted on a support 17. This encounter with the baffle plate substantially reduces the suction effect. The gas mixture then enters a mixing chamber 18 through the opening 14 between the baffle plate 16 and the cylinder 15. The gas mixture is forced out of the mixing chamber 18 through approximately eight outlet bores 19 and through the central bore 20 of the flange 11 into the inner tube 3b of the double-walled tube 3.

Most of the gas mixture returns to the flue through the vent pipe 21 attached to the inner tube 3 and is discarded (see FIG. 1). Part of the gas mixture is pumped out of the double-walled tube 3 through the gas connection 6 and carried to a suitable gas analysis apparatus. The ventilation of the jet pump into the flue through the tube 21 makes it unnecessary to remove the whole of the gas mixture from the sampling device as well as considerably reducing the effect of pressure fluctuations on the efficiency of the apparatus.

The cylinder 15 and baffle plate support 17 are assembled as shown in FIG. 2 and fixed into position by abutments before the jet pump cylinder 9 is screwed into the flange 11. The same applies to the nozzle head 13, which is inserted into the cover 8 before the cover is screwed onto the jet pump cylinder 9.

1.3 Example of dimensions

In one particular example, a degree of dilution of 1:155 is obtained with a jet pump dilution sampling device of the following dimensions:

| | |
|---|---|
| Bore 12 in nozzle head 13 | 1 mm diameter |
| Nozzle head 13 | 10 mm diameter |
| Intake suction opening 14 | 13 mm diameter |
| Baffle plate 16 | 20 mm diameter |
| Rate of flow of carrier gas | 517 litres per minute |
| Removal of gas sample | 30 litres per hour |

The nozzle head 13 projected by 2.9 mm over the internal edge of the opening 14 of cylinder 15 into the mixing chamber 18. The distance of the baffle plate 16 from the nozzle head 13 was 0.65 mm. The dimensions were optimised to produce minimum dependence of the degree of dilution on the rate of flow of carrier gas.

2. Dilution sampling device operating on the principle of diffusion 2.1 Principle The physical effect of diffusion may be utilised for diluting the gas to be analysed. Gas diffusion takes place when the concentration (partial pressure or partial density) of the gas varies from one place to another. Gases in a mixture behave approximately as if each were present on its own. Dilution is carried out on the following principle: Carrier gas free from gas to be analysed flows uniformly under pressure through an opening (e.g. a slot) into a flue (or the like). This opening is connected to a mixing chamber. Owing to the differing partial pressures of the components in the gas to be analysed as between the flue and the mixing chamber, the component to be measured diffuses into the mixing chamber against the stream of carrier gas. A stream of carrier gas containing diluted component to be measured can then be removed from the mixing chamber.

Very high dilutions of from $1:10^3$ to $1:10^6$ or higher can be obtained on this principle. The degree of dilution is proportional to the rate of diffusion and therefore depends on the stream of carrier gas, the surface area of the opening into the mixing chamber and the difference between the partial pressures of the component to be measured in the gas for analysis (flue) and the carrier gas.

2.2 Example

An example of a dilution device operating on the principle of diffusion is shown in FIG. 3 in which a dilution sampling device mounted on suitable supports is directly placed in the stream of exhaust gas. In the sampling device is a bore 23 (with an internal screw thread) for the connection of the carrier gas conduit. The carrier gas flows from the bore 23 through a bore 24 in a body 22 of the sampling device to an aperture ring 25 which has a semi-circular groove 26 for uniform distribution of the carrier gas to approximately 20 bores 27 (in the ring 25). The carrier gas is thereby caused to flow uniformly from all the bores 27 of the ring 25 into the conical gap 28 which tapers towards an annular outlet gap 29. The gap 28 is formed by the body 22 of the sampling device and a slit body 30 and at its outlet it has about the same size as the outlet gap 29. The slit body 30 is screwed to the body 22 of the sampling device. The carrier gas flows at high velocity from the gap 28 against the circular closure plate 31 which is fixed to the body 22 by the screw 32. Since only a small quantity of gas is sucked from the mixing chamber 33 through the bores 34, 34' and 35 by a pump, most of the carrier gas flows at high velocity into the flue through the outlet gap 29. This gap is thereby swept substantially free from particles of soot and dirt so that its cross-section does not vary. Since only a small part of the gas to be analysed is sucked out of the mixing chamber, the mixing chamber gap 36 formed by the body 22 of the sampling device and the carrier plate 31 may be smaller than the outlet gap 29. If the concentration of a component of the gas to be analysed is higher on the outside (in the flue) than in the carrier gas or in the mixing chamber 33, this component will diffuse through the outlet gap or diffusion gap 29 into the mixing chamber 33. The gas to be analysed is pumped off through the bores 34, 34' and 35 and carried to a suitable gas analyser.

2.3 Example of dimensions

In one example, the rate of flow of carrier gas was approximately 100 litres per hour and the gas to be analysed was drawn off at the rate of about 20 litres per hour. The outlet gap 29 and gap 28 (at the outlet point) were 0.4 mm in width and the gap 36 was 0.3 mm.

3. Dilution sampling device operating on the principle of periodic dilution 3.1 Principle In another embodiment, dilution is achieved by the periodic increase in size of a mixing chamber. This periodic increase in size causes exhaust gas to be drawn into the mixing chamber where it is mixed with a carrier gas which is free from the gas to be analysed. The gas to be analysed (mixture of carrier gas and exhaust gas) is drawn out of the mixing chamber and carried to a suitable gas analyser. The carrier gas which is at a higher pressure than the gas in the flue normally flows into the flue. During an intake stroke (increase in volume of mixing chamber), a certain amount of exhaust gas enters the mixing chamber if the increase in volume per intake stroke is greater than the quantity of carrier gas supplied during this time. To return to the starting position, the volume of the mixing chamber is reduced. If this reduction in volume is so rapid that the velocity of outflow through the intake aperture is suddenly increased, this aperture is swept free from dirt (flushing stroke). The degree of dilution of the exhaust gas depends on the rate of supply of carrier gas, the rate at which the gas to be analysed is sucked off and the change in volume of the mixing chamber per intake stroke. Degrees of dilution of from 1:5 to 1:500 can be achieved according to the adjustment of these parameters.

3.2 Example

The example of a dilution device operating on the principle of periodic dilution by change in the volume of a mixing chamber is shown in FIG. 4. This dilution sampling device can be mounted on a suitable support so that it lies in the stream of exhaust gas in a flue.

The body 22 of the sampling device has a bore 23 therein with internal threading for the connection of a carrier gas conduit thereto. The carrier gas flows from the bore 24 in the body 22 to an apertured ring 25. This ring 25 has a semi-circular groove 26 for the uniform distribution of the carrier gas to approximately 20 apertures 27 (in the ring 25). The carrier gas therefore flows substantially uniformly from all the bores 27 of the ring 25 into the conical gap 28 which tapers towards the annular outlet gap 29 (intake aperture). The gap 28 is formed by the body 22 of the sampling device and the slit body 30 which is screwed to the body 22. The size of the gap 28 at its outlet point is equal to or smaller than the outlet gap 29. The carrier gas flows at high velocity from the gap 28 against the circular closure disc 31 which is fixed to the body 22 of the sampling device by the screw 32. During an intake stroke, the volume of the mixing chamber 33 is increased by the volume $\Delta V$ (corresponding to the piston stroke) by the piston 37 which communicates with the cylinder chamber 39 through from four to six bores 38. All the carrier gas flowing through the gap 28 during the intake stroke and a certain amount of exhaust gas should be sucked into the mixing chamber 33 through the gap 36. The volume per unit time sucked in during the intake stroke should therefore be greater than the rate of flow of carrier gas through the outlet gap 29. The gas in the mixing chamber 33 (pure carrier gas or, after an intake stroke, a mixture of carrier gas and exhaust gas) is continuously pumped out of the mixing chamber through the bores 40 and 41 and carried to a suitable gas analyser. In the operating states between intake strokes, the carrier gas flows at high velocity from the gap 28 into the flue through the outlet gap 29 and prevents deposition of particles of dust and soot. An additional cleaning effect can be obtained, as already mentioned above, by sudden reduction of the stroke volume during the flushing stroke.

3.3 Example of dimensions

In one particular embodiment, a degree of dilution of 1:100 was obtained with a dilution sampling device of the following dimensions:

| | |
|---|---|
| Outlet Gap 29 | 0.4 mm |
| Gap 28 | 0.1 mm |
| Gap 36 | 0.3 mm |
| Rate of flow of carrier gas | 10 litres per hour |
| Rate of flow of gas to be analysed | 3.3 litres per hour |
| Diameter of piston 37 | 8 mm |
| Stroke of piston 37 | 40 mm |
| Stroke frequency of piston 37 | ½ strokes per second |

Gaps 28, 29 and 36 may be made much larger if the rate of flow of carrier gas is correspondingly increased.

The gas analysers used may be, for example, electrochemical gas detectors of the kind described in German Patent Specification No. 1773795. Non-dispersive IR analysers may also be suitable in other cases. The choice of gas analyser depends in any individual case on the component to be measured in the exhaust gas. No new problems arise in connection with the dilution sampling devices described above and therefore no detailed description of gas analysis apparatus has been given here.

What we claim is:

1. A method for the removal of samples for the purpose of analysis from a stream of exhaust gas, wherein the stream of exhaust gas is diluted with a carrier gas which is free from the gas to be analysed before the sample is removed from the stream of exhaust gas.

2. An apparatus for the removal of samples for the purpose of anlaysis from a stream of exhaust gas, comprising means for diluting the stream with a carrier gas including a jet pump through which the carrier gas flows and in which the stream of exhaust gas passes over intake apertures therein whereby the carrier gas in the jet pump draws a sample of the exhaust gas from the stream of exhaust gas and is mixed with it, means for removing the sample from the diluted stream, and means for conveying the sample to an analyzer comprising a discharge conduit connected to the jet pump.

3. An apparatus for the removal of samples for the purpose of analysis from a stream of exhaust gas comprising means for diluting the stream with a carrier gas including a mixing chamber having at least one aperture through which exhaust gas diffuses into the mixing chamber, and a carrier gas conduit connected to the mixing chamber which is at a higher pressure than the main stream of exhaust gas when in use, means for removing the sample from the diluted stream, and means for conveying the sample to an analyzer comprising a gas discharge conduit connected to the mixing chamber.

4. An apparatus for the removal of samples for the purpose of analysis from a stream of exhaust gas comprising means for diluting the stream with a carrier gas including a mixing chamber having at least one intake aperture through which exhaust gas is sucked into the mixing chamber from the main stream, a periodically operating piston pump connected to the mixing chamber so that the volume of the mixing chamber varies periodically with the volume of the cylinder and, a carrier gas supply conduit connected to the mixing chamber which is at a higher pressure than the stream of exhaust gas when in use, means for removing the sample from the diluted stream, and means for conveying the sample to an analyser comprising a gas discharge conduit connected to the mixing chamber.

* * * * *